United States Patent
Frey et al.

(10) Patent No.: US 7,517,360 B2
(45) Date of Patent: Apr. 14, 2009

(54) SYSTEM FOR AUTOMATICALLY INFLATING TEMPERATURE REGULATED BLANKETS AND A BLANKET FOR COUPLING TO THE SYSTEM

(75) Inventors: William E. Frey, Kingston, MA (US); Joseph Pierre, Brockton, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 711 days.

(21) Appl. No.: 11/080,481

(22) Filed: Mar. 16, 2005

(65) Prior Publication Data
US 2006/0212102 A1    Sep. 21, 2006

(51) Int. Cl.
*A61F 7/00* (2006.01)
(52) U.S. Cl. .......................... 607/104; 607/96; 607/108
(58) Field of Classification Search ................ 67/96–98, 67/104–112
See application file for complete search history.

(56) References Cited

U.S. PATENT DOCUMENTS

| | | | |
|---|---|---|---|
| 5,300,098 A | 4/1994 | Philipot | |
| 6,259,074 B1 | 7/2001 | Brunner et al. | |
| 7,220,273 B2 * | 5/2007 | Van Duren et al. | ............ 607/96 |
| 2002/0058974 A1 | 5/2002 | Van Duren et al. | |

* cited by examiner

*Primary Examiner*—Roy D Gibson
(74) *Attorney, Agent, or Firm*—Louis Woo

(57) ABSTRACT

A convective warmer to which blankets of different dimensions may be connected is capable of providing air to the various blankets at flow rates that optimally inflate those blankets to achieve the optimal clinical result for the patients covered by those blankets. The blanket connected to the warmer may range from a full size adult warming blanket to a pediatric or neonate warming blanket. There is provided on each blanket a code, marking or marker, to be read by a sensor(s) provided at the outlet of the warmer, that identifies the type of blanket when the blanket is coupled to the warmer. Consequently, heated air may be automatically output by the warmer to the blanket at the appropriate flow rate of that blanket to optimally inflate the blanket without any need for intervention by a user. In addition to being used to control the flow rate of the heated air, the code from the blanket may also be used to control the temperature of the heated air to be input to the blanket.

34 Claims, 5 Drawing Sheets

BLANKET SPEED SELECTOR
ELECTRONIC CONTROL

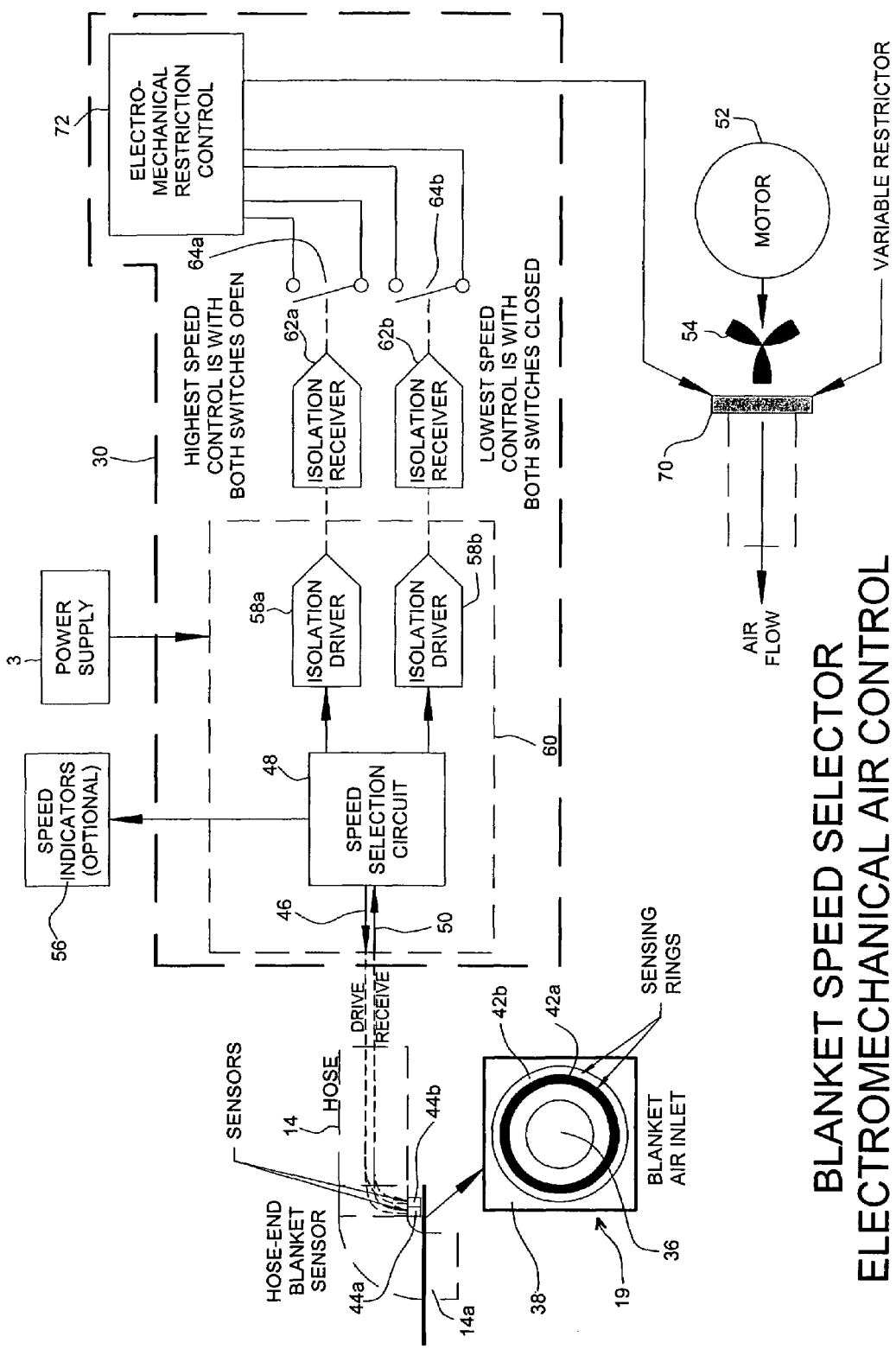

SYSTEM FOR AUTOMATICALLY INFLATING TEMPERATURE REGULATED BLANKETS AND A BLANKET FOR COUPLING TO THE SYSTEM

FIELD OF THE INVENTION

The present invention relates to warming blankets and to a system adapted to optimally inflate each of a plurality of warming blankets irrespective of the different dimensions of those blankets. The present invention more particularly relates to a system that automatically and optimally inflates a warming blanket when the blanket is coupled to the system.

BACKGROUND OF THE INVENTION

To hypothermically warm a patient, a convective warmer to which a warming blanket is connected is used. There are various convective warming blanket types that exist in the market today. The various blankets have different dimensions. Prior to the instant invention, a convective warmer, such as the current Level 1 Equator™ warmer, operates at only one speed, so that the same amount of air is output from the warmer irrespective of the size of the blanket connected to the warmer.

Insofar as the different blankets have different sizes, as for example from a full adult size blanket to a neonate blanket, and those blankets have different exhaust capabilities, the existing convective warmers such as for example the aforenoted Level 1 Equator™ system use differently sized outlet hoses adapted to mate with the differently sized blankets. For example, for a regular adult size blanket, a regular outlet hose is used. However, if the convective warmer were to be used to provide heated air to a pediatric warming blanket, which has a smaller dimension than a regular adult blanket, a special hose has to be fitted to the convective warmer so that a portion of the heated air is either blocked or bypassed from the blanket. This is due to the fact that a full size adult blanket requires a higher air flow and thus more volume of air in order to be inflated with the proper pressure, with the heated air coming out of the various holes or slits from the blanket to warm the patient. On the other hand, for a smaller warming blanket such as for example a pediatric blanket, the same amount of air input to the blanket, if possible, will over inflate the blanket. As a result, to inflate the pediatric blanket, a different hose has to be configured for the outlet of the convective warmer to bypass a portion of the output air so that the pediatric blanket could be properly inflated, and the proper output of heated air provided to warm the child patient covered by the blanket.

In co-pending applications entitled "System for Providing Actuated Optimal Inflation to Multiple Temperature Regulated Blankets and Method Therefor" and "System for Providing Optimal Inflation to Multiple Temperature Regulated Blankets and Method Therefor", both filed on Feb. 18, 2005 and assigned to the same assignee as the instant application, systems for inflating patient warming blankets of different dimensions at respective optimal flow rates are disclosed. The '0033 system requires the actuation of at least one switch for activating the system. In the '0034 systems, a sensor provided at the outlet at the system provides a feedback for controlling the flow rate of air to inflate the blanket. For such a feedback system, an expensive sensor, and an accompanying feedback circuit are required. The respective disclosures of the '0033 and the '0034 applications are incorporated herein by reference.

The present invention discloses a convective warmer that automatically inflates blankets of various dimensions optimally without requiring either switch actuation by a user or the expensive sensor and feedback system as disclosed in the above-referenced applications.

SUMMARY OF THE PRESENT INVENTION

The convective warmer of the instant invention is adapted to provide a fluid, such as for example air, at various flow rates, so that the differently dimensioned blankets may each be inflated optimally at a desired pressure. The provision of different flow rates by the convective warmer of the instant invention may be effected by using a variable speed blower, or a restricter or valve that has an opening which may be selectively controlled to enable a controlled amount of air to pass therethrough.

A first embodiment of the instant invention provides a patient warming blanket that has an inflatable body, an inlet or hose conduit for providing a fluid path to the body, and a code or marker positioned on the body for providing an indication of the flow rate of air required to optimally inflate the body. The blanket is to be used with a system that includes a convective warmer that has an outlet that allows the warmer to be mated to the inlet of the blanket for establishing a fluid path to the blanket, a heater for heating air in a plenum in the warmer, an air blower for directing the heated air to the outlet, and at least one sensor located relative to the outlet for reading or detecting the code on the blanket, and controller means for controlling the flow rate of the heated air provided to the outlet when the blanket is coupled to the warmer. The code on the blanket is read by the sensor, and a signal representative of the code is provided to the control means, which controls the inflation of the blanket in accordance with the flow rate as detected or sensed from the blanket.

A second embodiment of the instant invention comprises a system that has a patient warming blanket having an inflatable body, an inlet for providing a fluid path to the body, and a code positioned on the body for providing an indication of the flow rate of air required to optimally inflate the body. The system of the second embodiment further includes a convective warmer that has an outlet for mating to the inlet of the blanket, a heater for heating air in a plenum, an air blower adaptable to operate at variable speeds for directing the heated air at different flow rates to the outlet, at least one sensor located relative to the outlet for reading the code, and controller means for controlling the operating speed of the air blower, so that upon mating of the inlet of the blanket to the outlet of the warmer, the code on the blanket is read by the sensor at the warmer, and a signal representative of the code is provided to the controller means for selectively controlling the blower to operate at a selected speed to move the heated air to the blanket at the flow rate indicated by the code.

A third embodiment of the instant invention comprises a system that has a patient warming blanket including an inflatable body, an inlet for providing fluid path to the body, and a code positioned on the body for providing an indication of the flow rate of air required to optimally inflate the body. The third embodiment system further includes a convective warmer that has an outlet for mating to the inlet of the blanket, a heater for heating air in a plenum, an air blower for directing the heated air to the outlet, at least one sensor located relative to the outlet for reading the code, and a valve that can regulate the amount of heated air from the air blower to the outlet at a given time, so that when the blanket is coupled to the warmer, a signal representative of the code read by the sensor is used to control the valve for selectively regulating the output of the heated air at an amount that corresponds to the flow rate specified by the code.

The instant invention further includes a combination embodiment of an air convection warmer that has an outlet, a plenum in fluid communication with the outlet, a heater for heating air in the plenum, a blower for directing the heated air to the outlet, and a warming blanket connectable to the warmer for inflation. The blanket for the combination embodiment comprises a flow rate code positioned proximate to its inlet, and the warmer of the combination comprises at least one sensor located proximate to its outlet for detecting the code, such that when the inlet of the blanket is mated to the outlet of the warmer, the heated air is automatically supplied by the warmer at the flow rate indicated by the code to inflate the blanket.

The instant invention therefore utilizes a code or marking at the blanket to be connected to a warmer for identifying to the warmer the type of blanket that is coupled thereto so that the warmer can automatically output the heated air at an optimal flow rate to the blanket. The temperature of the air to be heated and fed to the blanket may also be regulated by the code.

BRIEF DESCRIPTION OF THE FIGURES

The instant invention will be best understood with reference to the following drawings wherein:

FIG. 5 is schematic diagram illustrating the present invention warming blanket coupled to a convection warmer as shown in FIG. 1 that has a variable valve operably controlled by an electromechanical flow control circuit.

DETAILED DESCRIPTION OF THE INVENTION

Figure 1:
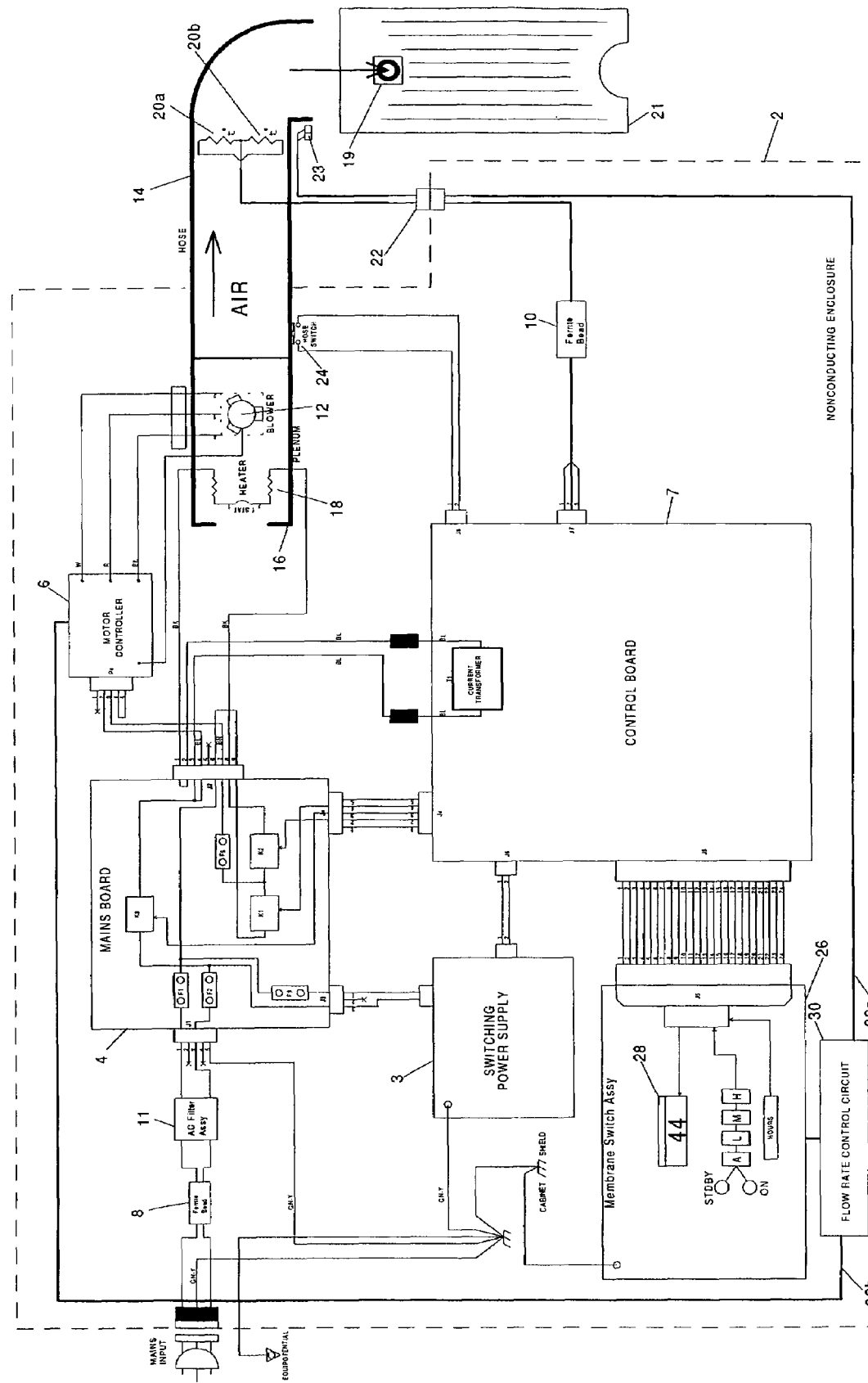
FIG. 1 is a schematic diagram of the overall system of the convection warmer of the instant invention.

With reference to FIG. 1, the convection warmer of the instant invention, shown enclosed by the enclosure designated by dotted line 2, includes a switching power supply 3 and a mains board 4. Mains board 4 includes fuses (f) and relays (k) that are used to supply power to both a motor controller 6 and a control board 7. To prevent conductive emission, a ferrite bead 8 is provided at the input of the AC power, and another ferrite bead 10 is provided at the output of the control board. An AC filter assembly 11 filters out transients from the AC power line.

Motor controller 6, with power provided from mains board 4, controls the operation of an air blower 12 which, for the purpose of this invention, may be considered a fluid mover that moves, directs or blows a fluid such as air to an outlet hose 14. Blower 12 is shown to be located in a plenum 16, which also has resided therein a heater 18 for heating the air being blown by the blower 12 to hose 14, which is connected to the outlet of the system. In practice, hose 14 may be considered the outlet of the convection warmer to which a warming blanket such as 21 is connected via its inlet 19.

Control board 7 contains, among other circuits, a power on and self-test circuit, a temperature control circuit that monitors thermistor 20a at the distal end of hose 14 to maintain the heated fluid at a given range of temperature for example approximately 36-44° centigrade, an under temperature indicator to indicate that the temperature is below a preset temperature and an overtemp supervisory circuit that monitors thermistor 20b at the distal end of hose 14 for ensuring that the temperature of the heater does not exceed a given temperature. The respective operations of most of these circuits are given in U.S. Pat. No. 6,259,074, the disclosure of which is incorporated by reference herein.

As shown, thermistors 20a and 20b are connected to control board 7 via a removable socket 22. Also connected to control board 7 is a hose switch 24 that indicates whether air hose 14 is attached to the system. If per chance hose 14 is removed or comes loose, hose switch 24 would detect that no air hose is attached, and the system will provide an alarm or an indication to the user that there is no air hose at, or that the air hose is not secured to, the outlet of the system.

Further provided in system 2 is a membrane switch assembly 26, which is the front panel of the system. It includes indicators for indicating whether the system is turned on or at a standby condition. Also provided on the front panel of the FIG. 1 embodiment are four switches A, L, M and N for indicating the ambient, low, medium and high temperatures, respectively, of the temperature of the air being heated by the heater. Although shown to be manually selectable from the front panel of the system, with the inventive patient warming blanket to be discussed infra, the temperature of the air to be heated by the heater may actually be controlled automatically, when the inventive blanket is coupled to the convective warmer of the instant invention. An indicator 28 is provided on the front panel to indicate the temperature at the distal end of hose 14.

For the instant invention, a flow rate control circuit 30 is in electrical communication with the membrane switch assembly 26. The flow rate control circuit 30 is also in electrical communication with motor controller 6 via line 32b and with socket 22 via line 32a. Controller 6 may control the speed with which air blower 12 operates, in the case where the blower is a variable speed blower, to be described infra with reference to the embodiment shown in FIG. 4. Alternatively, controller 6 may selectively control the opening of a valve or restrictor for controlling the amount of air to be output to the warming blanket at a given period of time, as will be discussed infra with the embodiment of FIG. 5. The variable speed air blower and the selectively controlled restrictor embodiments are respectively disclosed in the above-noted incorporated by reference '0033 and '0034 co-pending applications.

Figure 2:
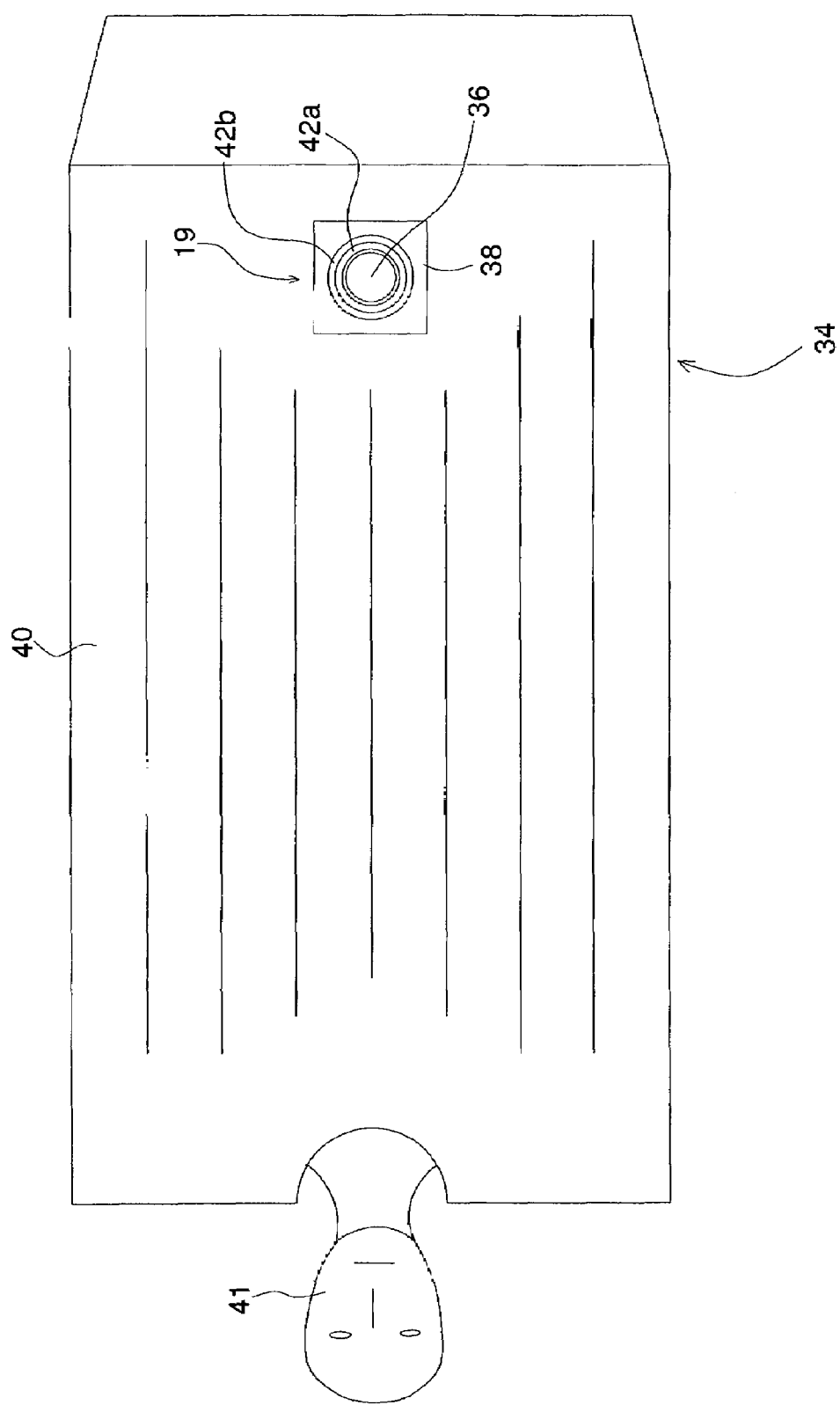
FIG. 2 shows an exemplar patient warming blanket of the instant invention.

FIG. 2 is a plan view of a patient warming blanket of the instant invention. Such blanket may be based on the blankets currently being sold by the assignee of the instant invention. For example, blanket 34 may be based on an adult full size blanket being manufactured by the assignee of the instant invention under manufacturing No. SW-2001. As shown, blanket 34 has an inlet 19 which has an opening 36 adapted to mate with outlet hose 14 of the convection warmer of FIG. 1. To provide support for opening 36, a piece of stiffener such as a cardboard 38, or similar material, is fixedly formed around opening 36. As is well known, blanket 34 has a body 40 that is inflatable, when fluid such as heated air is input to inlet 19, and more specifically through opening 36 of the inlet. Once optimally inflated, heated air would escape through slits or openings appropriately placed on the underside of the blanket for warming patient 41 covered by the blanket.

Figure 3:
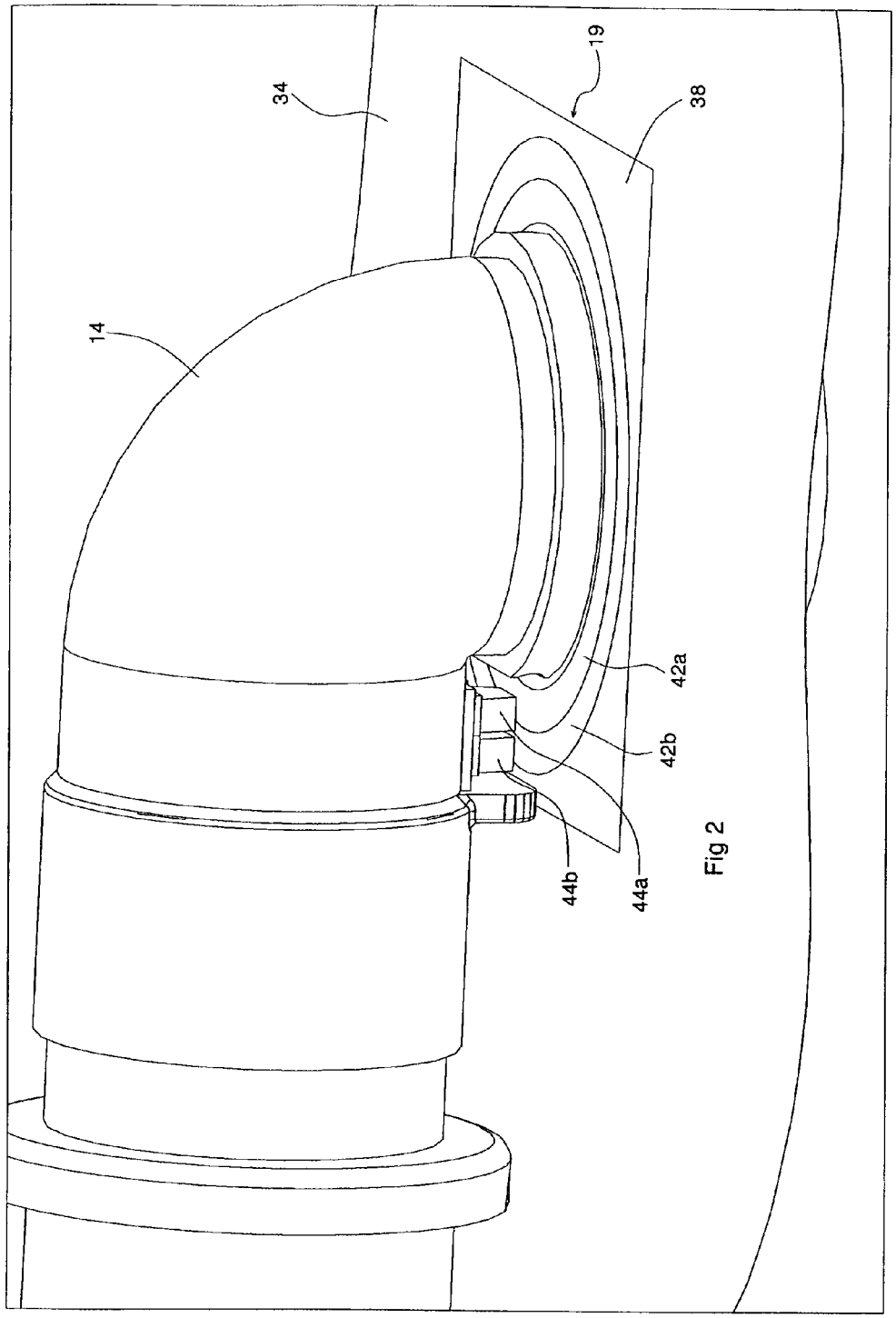
FIG. 3 is a drawing illustrating the mating of an outlet hose of the inventive convective warmer to an inlet opening of an inventive patient warming blanket.

For the blanket of the instant invention, a code or marker is provided on the blanket to provide an indication of the flow rate that is necessary to optimally inflate the blanket, and by implication the type of blanket it is, i.e., an adult, pediatric of neonate blanket. For the FIG. 2 exemplar blanket, the code is shown in the form of concentric circles 42a and 42b that surround opening 36. Although only two rings are shown, it should be appreciated that additional concentric rings may also be marked onto board 38. Concentric rings 42, for this embodiment, may be either light reflective, as when the ring is painted white, or light non-reflective, as when the rings are painted black or some other similar light absorbing color. The concentric rings may be printed directly onto board 38. Instead of the concentric rings, the code positioned on blanket 34 may consist of only those portions of the rings that are positioned directly under and detectable by the sensors when the blanket is coupled to the warmer (as illustrated in FIG. 3). The code may also be bar codes, magnetic stripes, or some other marker(s) that, when detected or sensed by the appropriate detector or sensor, would provide a signal that indicates the flow rate of air that is required to optimally inflate the blanket. As is conventionally known, the code or marker provided on the blanket of this inventions an inactive element that is not actively powered.

FIG. 3 is a perspective view of the mating or coupling of outlet hose 14 from the convection warmer of FIG. 1 to the inlet of a warming blanket such as for example blanket 34 shown in FIG. 2. For the FIG. 3 blanket, the concentric rings 42a and 42b are both shown to be light reflective. There is sensor means, in the form of a pair of sensors 44a and 44b that are mounted to hose 14 that, when the outlet hose from the convective warmer is properly mated to inlet 19 of the warming blanket, would be in proper superposed alignment over corresponding portions of rings 42a and 42b, respectively. The FIG. 3 sensors 44a and 44b each are optical sensors that can detect or sense the light reflected by the concentric rings 42a and 42b, respectively. When a ring is light non-reflective, for example when the ring is painted black, it is assumed that the sensor would output a one (1) signal. On the other hand, if a ring is made of light reflective material, or is painted to be light reflective such as for example white, the light reflected by the ring is detected by the sensor and a zero (0) signal is output by the sensor. The optical sensors may comprise infrared photo transistors For the FIG. 3 blanket, given that there are two sensors respectively superposing over two concentric rings, there are four possible scenarios or states that may be sensed by the pair of sensors provided at the outlet hose, and four corresponding signals possibly output by the sensors. Each of the output signals may in turn represent a given speed that the blower is to operate, or the amount of air to be let through by a valve, for inflating a warming blanket. For example, when both sensors detect light reflective rings (the rings being white rings), the signal output from the sensors would be 00. If ring 42a is white while ring 42b is black, then sensors 44a and 44b would detect a non-light reflective/light reflective state and would output a 01 signal to the control circuit of the convective warmer. If ring 42a is black and ring 42b is white, a 10 signal is sent to the convective warmer. Finally, if both rings are black, then a 11 signal is provided by the sensors to the control circuit of the convective warmer.

When in receipt of a 00 signal, assuming that a 00 detected state represents the lowest flow rate identified, the control circuit of the convective warmer would output the predetermined lowest amount of air per unit of time, either by slowing the speed of a variable speed blower (per the FIG. 4 embodiment) or narrowing the aperture of a variable controlled valve (per the FIG. 5 embodiment). The same process is repeated by the control circuit of the convective warmer upon receipt of the other signals (01, 10, 11) sent by the sensor means at the outlet hose. For explanation purposes, assume that a 00 signal corresponds to the lowest flow rate of air, at approximately 1100 ft/min, to be provided to the outlet of the warmer. A 01 signal designates a flow rate of air at approximately of 1300 ft/min. A 10 signal designates an air flow rate of approximately 1750 ft/min. And a 11 signal signifies the highest flow rate of air, at approximately 2100 ft/min, to be required by, and provided by the convective warmer to, the blanket.

There are a plurality of patient warming blankets. They include adult full size blanket, child size blanket and neonate blanket, for example. For the instant invention, assume that the code provided for the exemplar adult blanket is as shown in FIG. 3, i.e., that both concentric rings are black and therefore light is not reflected to the sensors. For a child blanket, assume that a black/white (10) state is detected by the sensors from the concentric ringed code positioned at the blanket, and a 10 signal accordingly is provided by the sensors to the control circuit of the convective warmer. In receipt of the 10 signal, the convective warmer outputs heated air at a flow rate of approximately 1700 ft/min, which is assumed to be the optimal inflation rate for the child blanket. As for a neonate blanket, assume that the concentric ring code thereon presents a white/black (01) state, and the sensors accordingly output a 01 signal to the control circuit of the convective warmer. The 01 signal causes the convective warmer to output heated air to the blanket at a flow rate of approximately 1300 ft/min to optimally inflate the neonate blanket. The lowest flow rate possible identifiable by the exemplar two ring embodiment code shown in FIG. 3 may be adapted to optimally inflate yet a smaller dimensioned blanket.

Although two concentric rings are shown in FIG. 3, it should be appreciated that, as noted previously, a code having a plurality of concentric rings greater than two may also be used. For example, if a three ring code is used, then the sensor means provided at the outlet of the warmer may conceivably detect eight different states, with a corresponding number of output signals possible.

Although concentric rings are shown in the FIG. 3 embodiment, it should be appreciated that other types of codes may also be used. Such codes may include bar codes, magnetic rings or magnetic stripes provided proximate to the inlet of the patient warming blanket. Of course, depending on the type of code, marker or marking that is used, a corresponding type of sensor is to be mounted proximate to the outlet of the convective warmer. For example, an optical scanner may be used for scanning a bar code, while a magnetic sensor may be used to sense magnetic stripes or rings provided on the blanket. Thus, in the case where a code that comprises a plurality of concentric magnetic rings is provided on the blanket, a magnetic sensor that includes a corresponding number of magnetic sensors, for example Hall Effect transistors, may be provided at the outlet of the warmer to detect the respective states of magnetization of the magnetic rings.

In addition to being used to control the flow rate of the heated air supplied to the blanket, the signal detected by the sensor means from the blanket may also be used to control the temperature of the heated air. For example, a pediatric blanket, and more specifically the child being covered by the pediatric blanket, may require a lower temperature warming than an adult covered by an adult blanket. Thus, upon detection of a pediatric blanket, the signal fed to the control circuit of the convective warmer would also control the heater of the warmer to heat the air at a lower temperature, for example lowered from 44° C. for an adult blanket to approximately to 40° C. for a pediatric or a neonate blanket. This is assuming that the convective warmer was previously used for an adult blanket. Of course, if the convective warmer had previously been used with a neonate blanket, and the temperature of the heated air is already at 36° C. to 40° C., then the temperature of the heated air would stay at the same temperature when a neonate or pediatric warming blanket is coupled to the warmer.

Figure 4:
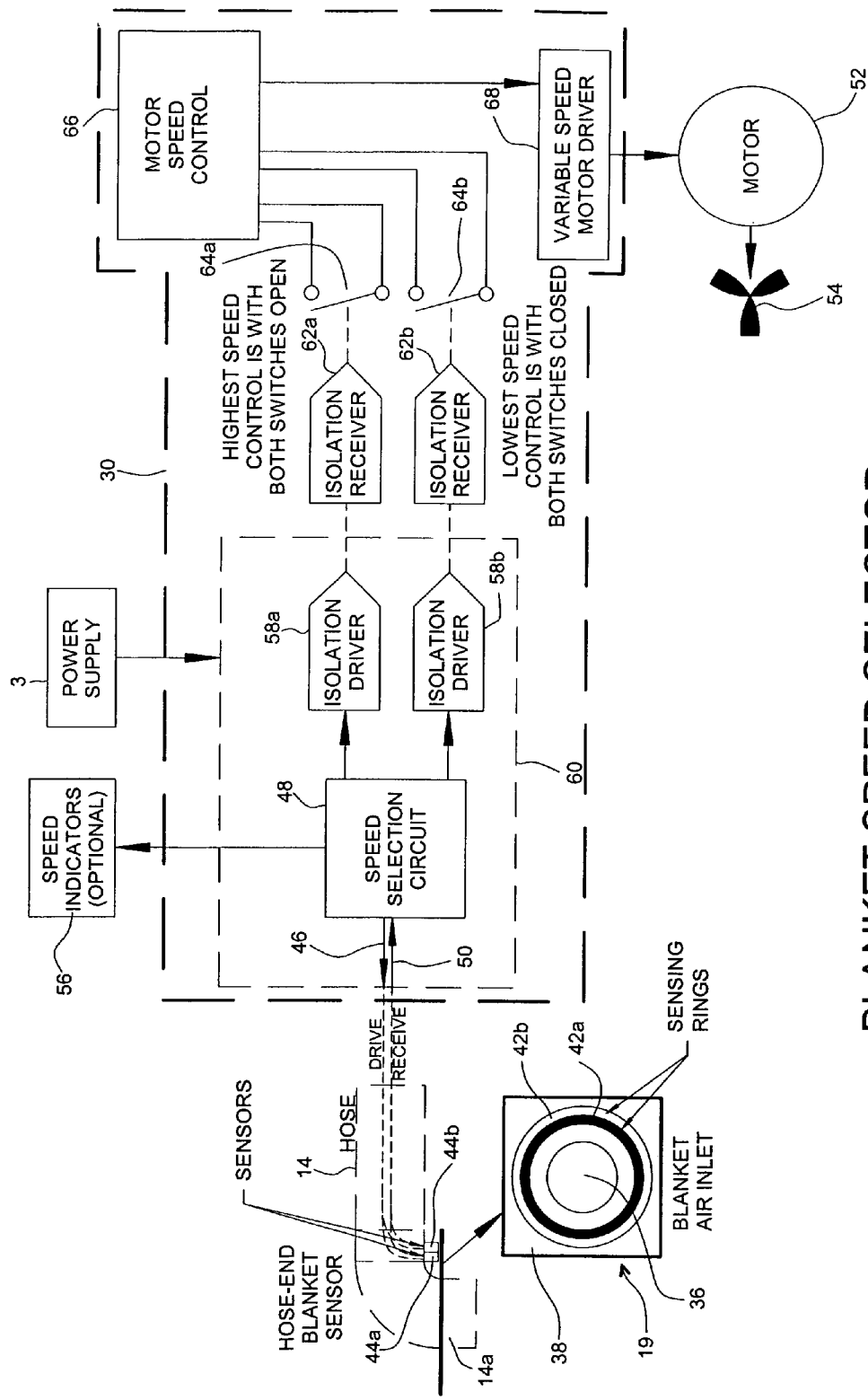
FIG. 4 is a block diagram illustrating the present invention patient warming blanket coupled to a convective warmer system as shown in FIG. 1 that has a variable speed blower operated by an electronic flow control circuit.

FIG. 4 illustrates the control circuit and the variable speed motor it drives for controlling the flow rate of the heated air to be provided by the convective warmer to the blanket, and the relationship between the outlet of the convective warmer and the inlet of the blanket.

FIG. 5 illustrates the control circuit and the variable valve or restrictor the control circuit controls for controlling the flow rate of the heated air to be provided by an alternate convective warmer, and the relationship between the outlet of that convective warmer and the inlet of the blanket.

With specific reference to FIG. 4, inlet 19 of a patient warming blanket is shown to include support 38 for the opening 36 of the inlet. Shown on support 38 surrounding opening 36 are two concentric rings 42a and 42b. For the embodiment shown in FIG. 4, ring 42a is a black or light non-reflective ring while ring 42b is a white or light reflective ring. Together, concentric rings 42a and 42b may be considered as a code or marker positioned proximate to the inlet 19 of the patient warming blanket.

To be mated to inlet 19 of the warming blanket is end 14a of hose 14. For the instant invention, hose 14 may also be considered as the outlet of the convective warmer. As shown, sensors 44a and 44b are mounted to a portion of hose 14 so that they will superpose over corresponding portions of rings 42a and 42b, respectively, when end 14a of the hose is mated to opening 36 of inlet 19 of the blanket. Sensors 44a and 44b are powered by the control circuit 30, indicated by the dotted line in the FIG. 4 embodiment, and more specifically by the speed selection circuit 48 via line 46. The signals output from sensors 44a and 44b in turn are fed via line 50 to speed selection circuit 48 within control circuit 30. As its name implies, speed selection circuit 48 in essence selects the speed with which to actuate the motor 52 for driving fan 54, which in turn directs the heated air to outlet 14 for input to the warming blanket. An optional speed indicator(s) 56 may be provided on the convective warmer of FIG. 1, for example on panel 26 thereof, for providing to the user an indication of the speed with which motor 52 is rotating for blowing air to inflate the blanket.

The output of the speed selection circuit 48 is provided to a pair of insolation drivers 58a and 58b, if needed. Speed selection circuit 48 and isolation drivers 58a and 58b may be considered, for the FIG. 4 embodiment, a sub-control circuit 60. The power for the components within sub-control circuit 60 is provided by power supply 3. The outputs of the optional isolation drivers 58a and 58b are provided to isolation receivers 62a and 62b, respectively. By utilizing isolation drivers and receivers, the speed selection circuit 48 within sub-control circuit 60 is isolated from transient voltages from the A/C line, should it be necessary. For the FIG. 4 embodiment, as well as the to be discussed FIG. 5 embroilment, since it is assumed that only four different states are detectable and four corresponding speeds are used, only one pair of isolation drivers/isolation receivers are illustrated for receiving the output from speed selection circuit 48.

The respective signals output from the isolation receiver 62a and 62b are fed to switches 64a and 64b which, in combination provide four possible signals to motor speed control 66, which may be represented by motor control 6 in the overall view of the convection warmer of FIG. 1. Motor speed control 66 has its output provided to a variable speed motor driver 68, which in turn controls the speed of motor 52 for driving fan 54.

As was discussed earlier, for the embodiment of FIG. 4, depending on the state of rings 42a and 42b, i.e., whether each of those rings is light reflective or light non-reflective, the rotational speed of motor 52, which effects the flow rate of air being provided to outlet 14, is controlled. Thus, assuming that an adult blanket such as that shown in FIG. 2 has the black/black code at its inlet, and further assuming that such black/black code provides an indication to the convective warmer that a high speed (2100 ft/min) flow rate of air is required to optimally inflate the blanket, then upon mating of outlet 14 of the convective warmer to inlet 19 of the blanket, the code at the inlet provides a signal (11), via the sensors, to the control circuit 30 of the convective warmer that it should drive motor 52 to operate at a rotational speed that would direct the heated air to the blanket at a flow rate of approximately 2100 ft/min, so that the warming blanket may be optimally inflated.

On the other hand, if a neonate blanket were coupled to the convective warmer, and the code provided at the inlet of the neonate blanket is white/black, assuming that such (01) code designates an air flow rate of approximately 1300 ft/min, then control circuit 30 will instruct motor 52 to operate at a rotational speed that would direct the heated air to inflate the neonate blanket at a flow rate of 1300 ft/min, so that the neonate blanket may be inflated at its desired optimal flow rate.

In addition to controlling the flow rate of the heated air being supplied to the blanket, the code at the inlet of the blanket may also instruct the control circuit of the convective warmer to vary the temperature at which the air is being heated at the plenum of the warmer, so that heated air of different temperatures may be provided to different blankets at respective corresponding optimal flow rates. For example, for a child covered by a pediatric blanket or an infant covered by a neonate blanket, the temperature of the heated air that escapes from the blanket for warming the child or infant should be at a temperature lower than that escaping from an adult blanket for warming an adult patient. Thus, instead of the approximately 44° C. air that is used to warm an adult patient, for a pediatric or neonate blanket, the temperature of the air is reduced to approximately 40° C. for the child or infant patient, when the sensor means at the outlet of the convection warmer detects that a pediatric or neonate blanket has been coupled thereto, for example by detecting the aforediscussed 01 code on the blanket.

FIG. 5 shows another embodiment of the convective warmer in which the flow rate of the heated air being supplied to the warming blanket is controlled by a variable valve or restrictor 70, which is controlled by an electromechanical restriction control 72. Aside from valve 70 and its control 72, all other components of the FIG. 5 embodiment are the same as those of FIG. 4 and are accordingly labeled the same.

For the FIG. 5 embodiment, motor 52 operates at a constant rotational speed for driving fan 54 to put out a constant air flow of approximately 2100 ft/min for example. The amount of air that is allowed to pass to outlet 14 is controlled by the variable size of an aperture (not shown) of valve 70. The size of the aperture of valve 70 is controlled by electromechanical restriction control 72, which receives as input the same signals as described earlier with respect to the FIG. 4 embodiment. Thus, depending on the signal it receives, which depends on the type of blanket being coupled to the convective warmer, via the sensors at outlet 14 detecting the code provided proximate to the inlet of the blanket, the appropriate dimensioned opening of the valve is effected by control 72 to allow the desired flow rate of heated air to be output to the blanket for optimally inflating the same. The increased back pressure that may result from the selectively controlled amount of air output to the outlet by restrictor 70 is either released to atmosphere or bypassed back to the inlet with an appropriate relief valve, not shown. As before, the temperature of the heated air may also be regulated by the code read by the sensor(s) at the convective warmer.

Although the code shown provided on the warming blankets are represented by concentric rings in FIGS. 3-5, it should be appreciated that other types of codes such as bar codes or magnetic stripes may also be provided so long as the appropriate type of scanner or detector is correspondingly provided at the outlet of the warmer.

The invention claimed is:

1. System, comprising:
   a patient warming blanket having
      an inflatable body,
      an inlet for providing a fluid path to said body;
      a non-actively powered code positioned on said body, said code when read by an appropriate sensor would identify at least the flow rate of air required to optimally inflate said body; and
   a convective warmer having
      an outlet for mating to said inlet to establish a fluid path to said blanket;
      a heater for heating air in a plenum of said warmer,
      an air blower for directing the heated air to said outlet,
      at least said sensor located relative to said outlet for reading said code;
      controller means for controlling the flow rate of the heated air provided to said outlet;
   wherein upon mating of said inlet of said blanket to said outlet of said warmer, said code is read by said sensor and a signal representative of the identified flow rate read by said sensor from said code is provided to said controller means to controllably inflate said blanket with the heated air at the flow rate indicated by said code.

2. System of claim 1, wherein said air blower is a variable speed air blower, and wherein said controller means controls the speed of said blower to direct air to said outlet in correspondence to said signal so that the heated air is provided to said blanket at the flow rate specified by said code.

3. System of claim 1, wherein said warmer further comprises a valve adapted to regulate the amount of air directed by said blower to said outlet, wherein said controller means actuates said valve to regulate the amount of heated air provided to said outlet at the flow rate specified by said code.

4. System of claim 1, wherein said warmer comprises a plurality of sensors and wherein said code comprises a plurality of concentric rings surrounding said inlet, said rings each being either reflective of light or non-reflective of light, said rings being detected by said pair of sensors when said inlet is mated to said outlet, and wherein the flow rate of the air supplied to said blanket is dependent on the combination of the light reflectiveness/non-reflectiveness of said rings as detected by said sensors.

5. System of claim 1, wherein said code comprises at least one magnetic stripe or marker positioned proximate to said inlet so as to be detectable by said sensor when said inlet is mated to said outlet.

6. System of claim 1, wherein said sensor comprises either an optical or magnetic scanner adaptable to detect said code.

7. System of claim 1, wherein the signal read by said sensor also controls said heater to adjust the temperature of the heated air to be supplied to said blanket.

8. System of claim 1, wherein said warmer comprises a plurality of sensors and wherein said code comprises a plurality of concentric rings surrounding said inlet, said rings each being either magnetic or non-magnetic, said rings being detected by said pair of sensors when said inlet is mated to said outlet, and wherein the flow rate of the air supplied to said blanket is dependent on the respective states of magnetization of said rings as detected by said sensors.

9. System, comprising:
   a patient warming blanket having
      an inflatable body,
      an inlet for providing a fluid path to said body, and
      a non-actively powered code positioned on said body, said code when read by an appropriate sensor would identify at least the flow rate of air required to optimally inflate said body; and
   a convective warmer having
      an outlet for mating to said inlet to establish a fluid path to said blanket,
      a heater for heating air in a plenum of said warmer,
      an air blower for directing the heated air to said outlet, said air blower adapted to operate at variable speeds to move the heated air at different flow rates, and
      at least said sensor located relative to said outlet for reading said code;
      controller means for controlling the operating speed of said air blower to move air to said outlet at selective flow rates;
   wherein upon mating of said inlet of said blanket to said outlet of said warmer, said code is read by said sensor and a signal representative of the identified flow rate read by said sensor from said code is provided to said controller means for selectively controlling said blower to operate at a selected speed to move heated air to said blanket via said outlet at the flow rate indicated by said code.

10. System of claim 9, wherein said code comprises a plurality of concentric rings surrounding said inlet, said rings being detected by a corresponding plurality of sensors of said warmer when said inlet is mated to said outlet.

11. System of claim 9, wherein said code comprises at least one magnetic stripe or marker positioned proximate to said inlet so as to be detectable by said sensor when said inlet is mated to said outlet.

12. System of claim 9, wherein said sensor comprises either an optical or magnetic scanner adaptable to detect said code.

13. System, comprising:
   a patient warming blanket having
      an inflatable body,
      an inlet for providing a fluid path to said body,
      a non-actively powered code positioned on said body, said code when read by an appropriate sensor would identify at least the flow rate of air required to optimally inflate said body; and
   a convective warmer having
      an outlet for mating to said inlet to establish a fluid path to said blanket,
      a heater for heating air in a plenum of said warmer,
      an air blower for directing the heated air to said outlet,
      at least said sensor located relative to said outlet for reading said code, and
      a valve for regulating the amount of heated air directed by said air blower to said outlet at a given time;
   wherein upon mating of said inlet of said blanket to said outlet of said warmer, said code is read by said sensor and a signal representative of the identified flow rate read by said sensor from said code is used to control said valve for selectively regulating the output of the heated air to said blanket at an amount that corresponds to the flow rate specified by said code.

14. System of claim 13, wherein said code comprises a plurality of concentric rings surrounding said inlet, said rings being detected by a corresponding plurality of sensors of said warmer when said inlet is mated to said outlet.

15. System of claim 13, wherein said code comprises at least one magnetic stripe or marker positioned proximate to said inlet so as to be detectable by said sensor when said inlet is mated to said outlet.

16. System of claim 13, wherein said sensor comprises either an optical or magnetic scanner adaptable to detect said code.

17. In combination, an air convection warmer having an outlet, a plenum in fluid communication with said outlet, a heater for heating air in said plenum, a blower for directing the heated air to said outlet, a warming blanket connectable to said warmer for inflation, said blanket having an inlet matable to said outlet of said warmer, said blanket further having a non-actively powered code positioned proximate to said inlet which when read by an appropriate sensor would identify the flow rate of air required to optimally inflate said blanket and the amount the air is to be heated, and said warmer further having at least said sensor located proximate to said outlet for detecting said code, wherein when said inlet of said blanket is mated to said outlet of said warmer, appropriately heated air is automatically supplied by said warmer at the flow rate identified by said code to inflate said blanket.

18. Combination of claim 17, wherein said code comprises a plurality of concentric rings surrounding said inlet, said rings each being either reflective of light or non-reflective of light, said rings being detected by a corresponding plurality of sensors of said warmer when said inlet is mated to said outlet, wherein the flow rate of the heated air supplied to said blanket is dependent on the combination of the light reflectiveness/non-reflectiveness of said rings as detected by said sensors.

19. Combination of claim 17, wherein said code comprises at least one magnetic stripe or marker positioned proximate to said inlet so as to be detectable by said sensor when said inlet is mated to said outlet.

20. Combination of claim 17, wherein said sensor comprises either an optical or magnetic scanner adaptable to detect said code.

21. Combination of claim 17, wherein said blower comprises a variable speed blower, said blower operating at a speed corresponding to the flow rate identified by said code for supplying the heated air to inflate said blanket.

22. Combination of claim 17, further comprising a valve operable in response to said code for regulating the amount of the heated air to be supplied from said warmer to inflate blanket.

23. Combination of claim 17, wherein said heater is regulated to change the amount of heat for heating the air so that the temperature of the heated air to be supplied to said blanket is adjusted in response to the detection of said code.

24. A blanket for use with a fluid temperature control system having a fluid outlet, comprising:
an inflatable body;
an inlet for mating to said outlet of said control system, said inlet providing a fluid path into said body; and
a non-actively powered code positioned on said blanket, said code when read by an appropriate sensor would identify to said control system the flow rate of the fluid to be supplied by said control system to inflate said body.

25. Blanket of claim 24, wherein said code comprises a plurality of concentric rings surrounding said inlet, said rings each being either magnetic or non-magnetic, said rings being detected by sensor means of said control system when said inlet is mated to said outlet, wherein at least the flow rate of the fluid supplied to said blanket is dependent on the respective states of magnetization of said rings as detected by said sensor means.

26. Blanket of claim 25, wherein said code provides a unique indication to said control system to supply the fluid to said blanket at a flow rate that optimally inflates said blanket.

27. Blanket of claim 25, wherein said code comprises a plurality of concentric rings surrounding said inlet, said rings each being either reflective of light or non-reflective of light, said rings being detected by sensor means of said control system when said inlet is mated to said outlet, wherein at least the flow rate of the fluid supplied to said blanket is dependent on the combination of the light reflectiveness/non-reflectiveness of said rings as detected by said sensor means.

28. Blanket of claim 27, wherein said sensor means comprises a plurality of sensors each adaptable to detect the light reflectiveness of a corresponding one of said rings.

29. Blanket of claim 27, wherein said concentric rings are adaptable to identify a plurality of different flow rates for supplying fluid to differently dimensioned blankets, wherein when said inlet of said blanket is mated to said outlet of said control system so as to couple said blanket to said control system, the concentric rings on said blanket are scanned by said sensors and the flow rate identified by said concentric rings of said blanket provides a signal to said control system that a particular one of said different flow rates is to be used for inflating said blanket.

30. Blanket of claim 25, wherein said code comprises at least one magnetic stripe or marker positioned proximate to said inlet so as to be detectable by sensor means of said control system when said inlet is mated to said outlet.

31. Blanket of claim 25, wherein said temperature control system comprises a convective warmer and wherein said fluid is air, said warmer having a heater for heating air in a plenum of said warmer independent of or in accordance with said code, and a blower for directing the heated air into said blanket at a flow rate in accordance with said code for inflating said blanket.

32. Blanket of claim 25, wherein said code is positioned proximate to said inlet of said blanket, and wherein said control system comprises at least one sensor positioned proximate to said inlet of said control system for detecting said code to supply the fluid to said blanket at the optimal flow rate for said blanket.

33. Blanket of claim 32, wherein said sensor comprises either an optical or magnetic scanner adaptable to detect said code.

34. Combination of claim 17, wherein said code comprises a plurality of concentric rings surrounding said inlet, said rings each being either magnetic or non-magnetic, said rings being detected by a corresponding plurality of sensors of said warmer when said inlet is mated to said outlet, wherein the flow rate of the heated air supplied to said blanket is dependent on the respective states of magnetization of said rings as detected by said sensors.

* * * * *